US012116399B2

(12) United States Patent
Zakas et al.

(10) Patent No.: US 12,116,399 B2
(45) Date of Patent: Oct. 15, 2024

(54) VON WILLEBRAND FACTOR PROTEINS FOR TREATING BLEEDING DISORDERS

(71) Applicants: QUEEN'S UNIVERSITY AT KINGSTON, Kingston (CA); KINGSTON HEALTH SCIENCES CENTRE, Kingston (CA); EMORY UNIVERSITY, Atlanta, GA (US); GEORGIA TECH RESEARCH CORPORATION, Atlanta, GA (US)

(72) Inventors: Philip Zakas, Cambridge, MA (US); David Lillicrap, Kingston (CA); Christopher Doering, Atlanta, GA (US); Eric Gaucher, Atlanta, GA (US); Caelan Radford, Seattle, WA (US); Harold Trent Spencer, Atlanta, GA (US)

(73) Assignees: Queen's University at Kingston, Kingston (CA); Kingston Health Sciences Centre, Kingston (CA); Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 487 days.

(21) Appl. No.: 16/760,206

(22) PCT Filed: Nov. 1, 2018

(86) PCT No.: PCT/CA2018/051389

§ 371 (c)(1),
(2) Date: Apr. 29, 2020

(87) PCT Pub. No.: WO2019/084691

PCT Pub. Date: May 9, 2019

(65) Prior Publication Data

US 2020/0347116 A1 Nov. 5, 2020

Related U.S. Application Data

(60) Provisional application No. 62/580,133, filed on Nov. 1, 2017.

(51) Int. Cl.

| | |
|---|---|
| ***C07K 14/745*** | (2006.01) |
| ***A61K 38/36*** | (2006.01) |
| ***A61P 7/04*** | (2006.01) |
| ***C07K 14/755*** | (2006.01) |
| ***C12N 15/86*** | (2006.01) |
| *A61K 38/00* | (2006.01) |

(52) U.S. Cl.
CPC .............. *C07K 14/755* (2013.01); *A61P 7/04* (2018.01); *C12N 15/86* (2013.01); *A61K 38/00* (2013.01); *C12N 2740/10043* (2013.01)

(58) Field of Classification Search
None
See application file for complete search history.

(56) References Cited

U.S. PATENT DOCUMENTS

| | | | | |
|---|---|---|---|---|
| 2012/0289468 A1* | 11/2012 | Barnett | A61P 7/00 | 435/69.6 |
| 2014/0357564 A1* | 12/2014 | Schulte | A61P 7/02 | 514/14.1 |
| 2015/0139953 A1 | 5/2015 | Gao et al. | | |

FOREIGN PATENT DOCUMENTS

| | | |
|---|---|---|
| WO | WO2016/123200 A1 | 8/2016 |
| WO | WO2018/208973 A1 | 11/2018 |

OTHER PUBLICATIONS

Johnsen, J.M, et al. 2013 Blood 122(4): 590-597. (Year: 2013).*
Nichols, T.C., et al. 2010 Thrombosis, article ID 461238: 11 pages. (Year: 2010).*
International Search Report and Written Opinion for corresponding International application No. PCT/CA2018/051389 filed on Nov. 1, 2018.
Zakas, P.M. et al., "Enhancing the pharmaceutical properties of protein drugs by ancestral sequence reconstruction", Nat. Biotechnol., vol. 35, pp. 1-13, (2017).
Zakas, P.M. et al., "Ancestral Sequence Reconstruction of Von Willebrand Factor Reveals Highly Conserved Structure/Function", Blood, vol. 130, p. 240, (2017).

* cited by examiner

*Primary Examiner* — Marsha Tsay
(74) *Attorney, Agent, or Firm* — Licata & Tyrrell P.C.

(57) ABSTRACT

A recombinant von Willebrand Factor (VWF) protein comprising one or more mutations and uses thereof are described. A recombinant protein complex comprising a von Willebrand factor sequence and one artificial Factor VIII sequence is described. A recombinant protein complex comprising a Factor VIII sequence and one artificial von Willebrand sequence is described. A recombinant protein complex is described that includes one artificial von Willebrand factor sequence and one artificial Factor VIII sequence. Also described are nucleic acid sequences and a vector encoding a VWF sequence and a pharmaceutical composition for inducing blood clotting that includes a VWF protein.

14 Claims, 10 Drawing Sheets

Specification includes a Sequence Listing.

VON WILLEBRAND FACTOR PROTEINS FOR TREATING BLEEDING DISORDERS

RELATED APPLICATION

This application claims the benefit of the filing date of Application No. 62/580,133, filed Nov. 1, 2017, the contents of which are incorporated herein by reference in their entirety.

FIELD

The field of the invention is biomedical protein chemistry. More specifically, the field relates to nucleic acid constructs and proteins that affect coagulation. The nucleic acid constructs may be used in gene therapy treatment of individuals with bleeding disorders such as von Willebrand disease and hemophilia A. The proteins may be used to treat individuals with bleeding disorders such as von Willebrand disease and hemophilia A. The invention also relates to complimentary drug treatments that enhance the gene therapy treatment.

BACKGROUND von Willebrand disease (VWD) and hemophilia A (HA) are the most prevalent and severe inherited bleeding disorders in the global population. The bleeding phenotype observed in both pathologies is characterized by joint inflammation and damage, soft tissue bleeds, and potentially lethal hemorrhages arising from qualitative or quantitative deficiencies in either von Willebrand factor (VWF) or coagulation factor VIII (FVIII), respectively. Treatment of hemophilia A is limited to exogenous protein replacement from either plasma or recombinant sources while VWD is treated with desmopressin, protein replacement, and in rare cases, platelet transfusions. VWF is a molecular chaperone for FVIII, prolonging the plasma half-life from 2 to 15 hours. As a result, VWD is also concomitant with decreased plasma FVIII concentrations. Mutations in either FVIII or VWF that reduce binding affinity result in increased FVIII clearance and a worsened bleeding phenotype. Therefore, understanding the FVIII-VWF binding interaction is pivotal to the development of novel therapies.

Bioengineering attempts to substitute VWF with more persistent chaperones such as albumin have been unsuccessful and efforts to improve FVIII pharmacokinetics with post-translational modifications (i.e. PEGylation, Fc fusion, etc.) have resulted in only marginal enhancements of half-life. These modifications reduce the clearance rate of unbound FVIII either by increasing protein recycling or antagonizing proteolytic cleavage and interaction with clearance receptors. However, these modifications have a negligible effect on FVIII in complex with VWF. The clearance rate of VWF remains the upper limit of FVIII therapeutics. Current bioengineering efforts recognize this and have shifted to extend VWF half-life with similar post translational modifications to the VWF molecule itself. In these engineering efforts, preservation of a strong FVIII-VWF binding affinity is paramount, as dissociated FVIII, regardless of modification, will be cleared more rapidly without VWF. Therefore, the goal of current bioengineering efforts is the development of a VWF molecule which demonstrates both equivalent or greater binding affinity to FVIII and prolonged half-life in circulation.

Clearance of VWF is actively mediated by the asialoglycoprotein receptor (ASGPR), lipoprotein receptor (LRP1), and Siglec-5, on the surface of macrophages and hepatocytes as well as CLEC4M on sinusoidal endothelial cells. Mutations affecting several canonical and non-canonical asparagine-linked glycosylation sites have been reported to potentiate VWF clearance. While clearance of VWF is largely mediated by N- and O-linked glycosylation, amino acid residue substitutions, including the R1205 Vicenza variant, also affect clearance rates. These observed substitutions occur throughout the D, A, and C-domains with the greatest concentration occurring in the D'D3 and A1 domains. These domains are also responsible for FVIII binding and platelet interaction through the GP1b complex. Novel VWF sequences which aim to reduce clearance within these domains are likely to interfere with FVIII binding or platelet activation inadvertently. The complexity of VWF multifunctionality coupled with limited structural information precludes most engineering efforts at the amino acid level.

Sequence Reconstruction (SR) is a platform technology for the engineering of complex proteins for which limited structural information exists. This methodology infers sequences of common ancestry from extant sequences using Bayesian inference. Distinguished from random or directed evolution, SR results in sequences with uniform functionality and, importantly, accounts for epistatic covariant effects. The result is a phylogenetic analysis of molecular evolution preceding modern orthologous molecules. The relatively few amino acid substitutions occurring between each sequence within a phylum provides significantly greater resolution than ortholog scanning. Biochemical characterization of the resulting proteins can be conducted following custom DNA synthesis.

Recently, SR was used to construct FVIII sequences within the class mammalia. This investigation resulted in the identification of a novel sequence (An53-FVIII) with high identity to human FVIII but demonstrated increased biosynthetic efficiency which directly translated into a promising adeno associated virus (AAV) gene therapy strategy. This study also identified specific residues responsible for increased stability of the FVIIIa molecule following thrombin activation as well as the functional epitope of an extremely potent FVIII inhibitor.

SUMMARY

In one aspect, the invention provides a recombinant von Willebrand Factor (VWF) protein comprising one or more mutations wherein one or more amino acids are substituted compared to SEQ ID NO: 11. In one embodiment of this aspect, at least one sequence is selected from SEQ ID NOs: 6 to 10 and 12 to 63. In one embodiment of this aspect, the at least one sequence is selected from An101-VWF (SEQ ID No. 6), An84-VWF (SEQ ID No. 8), An63-VWF (SEQ ID No. 10), An88-VWF (SEQ ID No. 7) or An70-VWF (SEQ ID No. 9), or variants thereof.

In one aspect, the invention provides a nucleic acid encoding the protein of any one of the above aspect or its embodiments. In one embodiment, the nucleic acid comprises SEQ ID No. 1, 2, 3, 4, 5, or a combination thereof.

In one aspect, the invention provides a pharmaceutical composition comprising a nucleotide of SEQ ID Nos. 1 to 5, or a combination thereof.

In one aspect, the invention provides a method of inducing blood clotting comprising administering an effective amount of the above pharmaceutical composition to a subject in need thereof.

In one aspect, the invention provides a composition comprising at least one recombinant protein, wherein the composition comprises a von Willebrand factor sequence and one artificial Factor VIII sequence, a Factor VIII sequence and one artificial von Willebrand sequence, or one artificial Factor VIII sequence and one artificial von Willebrand sequence. In one embodiment of this aspect, the artificial Factor VIII sequence is selected from SEQ ID No. 66 to 69, or a combination thereof. In one embodiment, the artificial von Willebrand sequence is selected from SEQ ID Nos. 6 to 10, 12 to 63, or a combination thereof.

In one aspect, the invention provides a method comprising administering the composition of any one of the above aspect or its embodiments. In one embodiment of this aspect, the proteins comprise a truncated factor VIII or von Willebrand factor sequence. In one embodiment of this aspect the proteins comprise two or more mutations.

In one aspect, the invention provides a method of inducing blood clotting comprising administering an effective amount of the pharmaceutical composition of the above aspect to a subject in need thereof.

In one aspect, the invention provides a method for treating a subject with a bleeding disorder, comprising administering an effective amount of the pharmaceutical composition of the above aspect to the subject. In an embodiment of the above methods, the subject is human. In one embodiment of this aspect, the bleeding disorder comprises hemophilia A or von Willebrand disease.

In one aspect, the invention provides a vector comprising a promotor nucleic acid sequence in operable combination with An-VWF nucleic acid sequence of SEQ ID No. 1, 2, 3, 4, 5 or a combination thereof, a combination of An-VWF nucleic acid sequence of SEQ ID No. 1, 2, 3, 4, 5 together with An-FVIII nucleic acid sequence, a combination of An-VWF nucleic acid sequence of SEQ ID No. 1, 2, 3, 4, 5 together with FVIII nucleic acid sequence, or a combination of VWF nucleic acid sequence of SEQ ID No. 11, together with An-FVIII nucleic acid sequence.

In one embodiment, the An-FVIII nucleic acid sequence is SEQ ID Nos. 64, 65 or a combination thereof. In an embodiment of this aspect, the vector comprises a retrovirus.

In one aspect, the invention provides a pharmaceutical composition comprising the protein of any one of the above aspects or embodiments or the vector of the above aspect, and a pharmaceutically acceptable excipient.

In one aspect, the invention provides an expression system comprising the vector of the above aspect. In one embodiment, the retrovirus is spumavirus, lentivirus, or adenovirus.

In one aspect, the invention provides an expression system comprising the vector of the above aspect.

BRIEF DESCRIPTION OF THE DRAWINGS

For a better understanding of the invention and to show more clearly how it may be carried into effect, reference will now be made by way of example to the accompanying drawings, wherein.

DETAILED DESCRIPTION

Definitions

Figure 1:
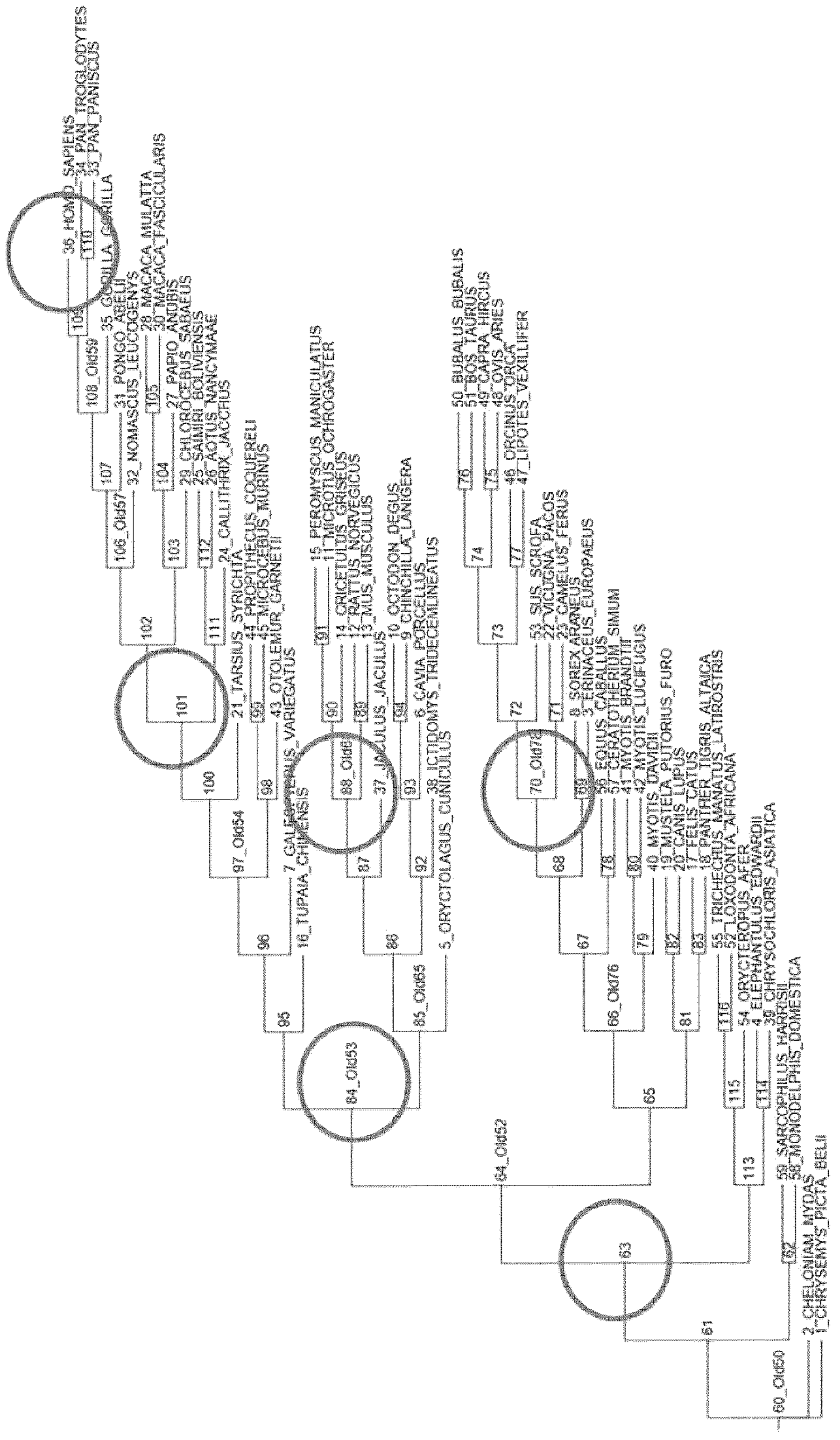
FIG. 1 shows a phylogenetic tree that was constructed for mammalian VWF genes using known amino acid sequences. Intermediary nodes that were reconstructed through gene synthesis are circled. These genes have been codon optimized for human cell expression and have been sub-cloned into the mammalian expression plasmid pCI-neo.

As used herein, a "non-naturally occurring" sequence is one for which no organisms produce or ever produced through the course of natural events. A protein is non-naturally occurring if one or more amino acids are substituted such that the entire amino acid sequence was never produced due to the course of natural events.

As used herein, "mutation" refers to an alteration in a nucleic acid sequence that results in an amino acid substitution in the corresponding protein when compared to the consensus human sequence, (i.e., cohVWF, SEQ ID NO: 11). A position of the amino acid substitution can be identified by reference to numerical positions within SEQ ID NO: 11 with or without reference to the protein having the propeptide. With regard to mutations, it is common to refer to the numbering system above wherein VWF does not contain the propeptide as it is typically cleaved during cellular processing. As used herein, a mutation refers to a mutation not found in the sequence for any known primates or mammals.

As used herein, "An-" denotes artificial number and indicates that the species (e.g., nucleotide or protein) to which it refers is non-naturally occurring or artificial.

The terms "protein" and "polypeptide" refer to compounds comprising amino acids joined via peptide bonds and are used interchangeably.

As used herein, "amino acid sequence" refers to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include post-translational modifications of the deduced amino acid sequences, such as amino acid deletions, additions, and modifications such as glycosylations, addition of lipid moieties, and disulfide linkages.

The term "nucleic acid" refers to a polymer of nucleotides, or polynucleotides. The term is used to designate a single molecule, or a collection of molecules. Nucleic acids may be single stranded or double stranded of self-complementary, and may include coding regions and regions of various control elements.

The terms "a nucleic acid sequence encoding" a specified polypeptide refers to a nucleic acid sequence comprising the coding region of a gene or in other words the nucleic acid sequence which encodes a protein. The coding region may be present in either a cDNA, genomic DNA, or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" in reference to a nucleic acid molecule refers to a nucleic acid molecule which is comprised of segments of nucleic acid joined together by means of molecular biological techniques. The term "recombinant" in reference to a protein or a polypeptide refers to a protein molecule which is expressed using a recombinant nucleic acid molecule.

The term "chimera" when used in reference to a polypeptide of polynucleotide refers to the expression product of two or more coding sequences obtained from different genes, that have been cloned together and that, after translation, act as a single polypeptide sequence such that the single or whole polypeptide sequence, or nucleotide sequence, is not naturally occurring. Chimeric polypeptides are also referred to as "hybrid" polypeptides. The coding sequences include those obtained from the same or from different species of organisms.

The term "heterologous nucleic acid" refers to a nucleic acid that is not in its natural environment (i.e., has been altered by the hand of man). For example, a heterologous nucleic acid includes a gene from one species introduced into another species. A heterologous nucleic acid also includes a gene native to an organism that has been altered in some way (e.g., mutated, added in multiple copies, linked to a non-native promoter or enhancer sequence, etc.). Heterologous viral nucleic acids are distinguished from endogenous viral genes in that the heterologous gene sequences are typically joined to nucleotide sequences comprising regulatory elements such as promoters that are not found naturally associated with the gene for the protein encoded by the heterologous gene or with viral gene sequences in the chromosome, or are associated with portions of the chromosome not found in nature (e.g., genes expressed in loci where the gene is not normally expressed).

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids or nucleotide (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro and cell free systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro and cell-free protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, *Nat. Biotechnol.*, 19, 751-755 and Asahara & Chong, *Nucleic Acids Research*, 2010, 38(13): e141, both hereby incorporated by reference in their entirety.

Embodiments

In practicing the embodiments described herein, many conventional techniques in cell biology, molecular biology, protein biochemistry, immunology, and bacteriology are used. These techniques are well-known in the art and are provided in any number of available publications, such as Current Protocols in Molecular Biology, Vols. I-III, Ausubel, Ed. (1997); Sambrook et al., Molecular Cloning: A Laboratory Manual, Second Ed. (Cold Spring Harbor Laboratory Press, Cold Spring Harbor, N.Y., 1989). Unless specifically defined herein, all technical and scientific terms used herein generally have the same meaning as commonly understood by one of ordinary skill in the art to which this invention belongs.

In the following descriptions of various embodiments of the invention, references to sequences and sequence listings are made. Those of ordinary skill in the art will readily appreciate that the invention is not limited to the specific sequences described, as many variants are possible without departing from the invention. For example, substitutions, mutations, deletions, and/or additions of one or more nucleotides or amino acids may be made, or may occur, without substantial effect on functional properties. Such a functional equivalent may have, for example, 60%, or 70%, or 80%, or 90%, or more sequence identity with a sequence described herein. Such functional equivalents are intended to be included in the embodiments of the invention.

As described herein, SR was used to generate artificial nucleotide VWF sequences ("An-VWF") with two objectives: i) to explore sequences for differential biochemical properties which could be therapeutically advantageous, and ii) to identify the functional variants responsible for observed biochemical differences.

Five mammalian An-VWF sequences were generated and characterized within the primate, rodent, and ungulate lineages derived from reconstruction of 59 extant mammalian sequences. These sequences display similar biosynthetic efficiencies, retain multimeric formation, FVIII binding, collagen binding, and platelet function, albeit to markedly variable degrees. Additionally, analysis revealed four sequences with prolonged half-lives in VWF deficient mice compared to human VWF, suggesting reduced association with murine clearance receptors. Together, these data identify novel sequences with therapeutically advantageous properties. These sequences may facilitate improved recombinant products and/or gene therapy strategies directly and may also enable the production of chimeric sequences with maximal identity to the human VWF sequence due to resolution of biochemically functional residues.

von Willebrand factor (VWF) is a large multimeric glycoprotein of critical importance for both primary and secondary hemostasis due to its role in platelet activation and stabilization of coagulation factor VIII (FVIII), respectively. Mutations affecting VWF synthesis, secretion, or function result in one of 6 distinct subtypes of von Willebrand disease (VWD) with mutations inhibiting FVIII binding classified as type 2N. Due to low circulating levels of plasma FVIII, type 2N patients can be misdiagnosed with hemophilia A. Because the clearance of FVIII is dominated by its association with VWF, and given recent evidence demonstrating an immuno-protective role of VWF for FVIII, understanding the molecular interaction between FVIII and VWF remains critically important for both hemophilia A and type 2N VWD therapeutic development. However, limited structural information remains a major limitation for rational design studies. Recently, SR was performed to infer the sequences of FVIII predicted to have existed throughout mammalian evolution. SR provides a platform for high-resolution mapping of sequential differences within a phylogeny while maintaining a high probability of retaining function. Sequential changes in the amino acid sequence of FVIII appears to have resulted in altered biochemical properties including biosynthesis and stability. It was also demonstrated that a previously characterized An-FVIII molecule with 95% identity to human FVIII, termed An53-FVIII (SEQ ID No. 66) exhibited a 2.5 to 5-fold increase in binding to human VWF relative to commercial recombinant FVIII products. The FVIII-VWF interaction was investigated through SR of VWF and through biochemical analysis. Without wishing to be bound by theory, the inventors suggest that although the FVIII-VWF association has remained a conserved function throughout evolution, changes in either protein have resulted in variable strengths of association, which can be utilized for therapeutic engineering purposes.

A phylogenetic tree was constructed for mammalian VWF and amino acid sequences predicted through Bayesian inference using 59 extant sequences. This allowed accurate prediction of the sequences extending beyond the class Mammalia. Of the resulting 50, 5 An-VWF sequences representing significant branch points in primate, rodent, and ungulate evolution were selected for synthesis de novo and subsequent biochemical characterization. All sequences, including an additional human (h) VWF cDNA, were human codon optimized (co). These sequences are predicted to span 105 million years of evolution and contain 81 to 364 amino acid substitutions (see FIG. 1 and Table 1).

Figure 2A:
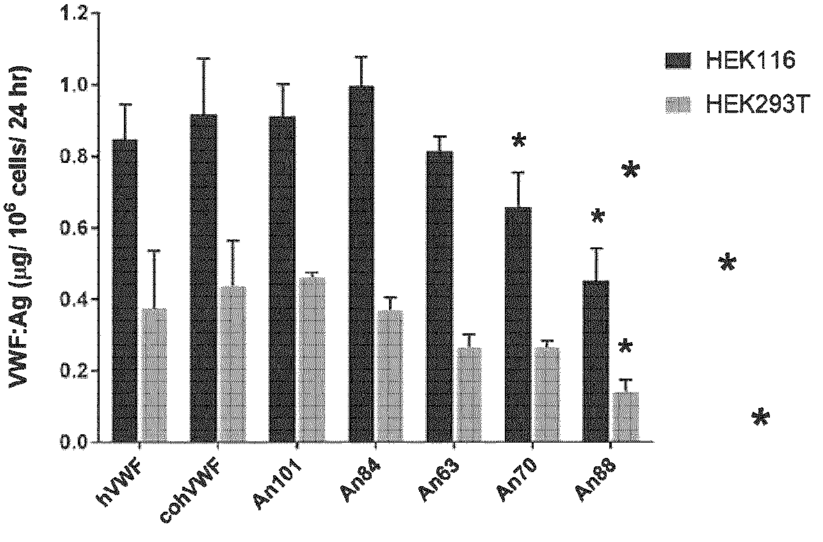
FIG. 2A shows VWF protein expression data where HEK116 and HEK293T cells were transiently transfected with VWF plasmid via polyethylenimine (PEI). Twenty-four hours after replacing DMEM media with serum-free opti-MEM, supernatant was assayed for VWF antigen via ELISA assay and shown normalized to cell count.
Figure 2B:
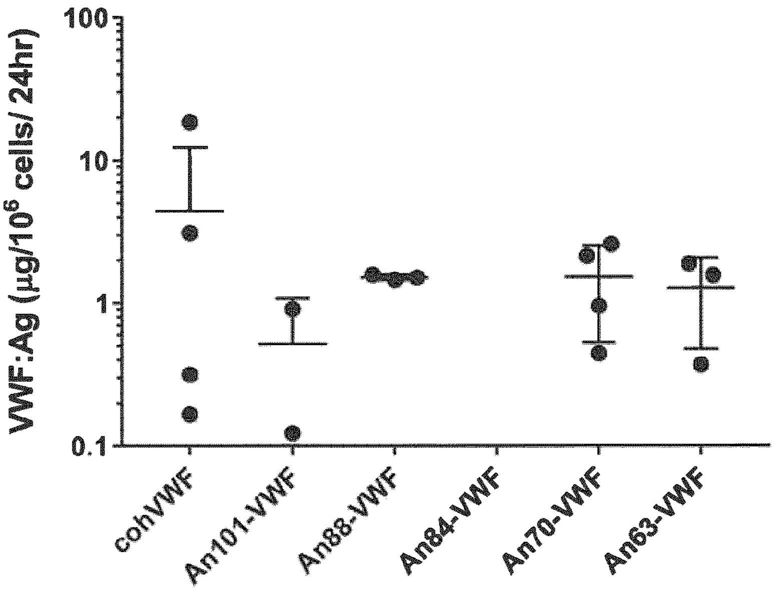
FIG. 2B shows protein expression data of stable HEK116 clones were generated using G418 selection following transfection of VWF plasmid with PEI. Clones were selected from each VWF treatment. Shown are the VWF expression levels as determined by ELISA and normalized to cell counts.
Figure 2C:
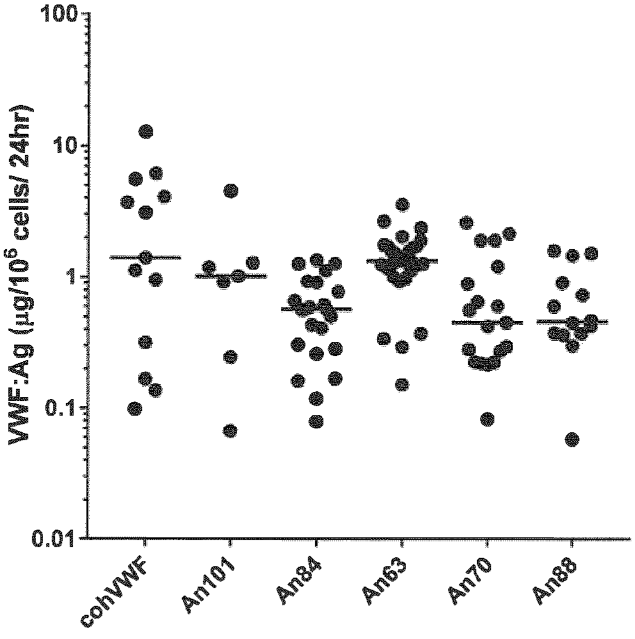
FIG. 2C shows protein expression data of stable HEK116 clones were generated using G418 selection following transfection of VWF plasmid with PEI. Clones were selected from each VWF treatment. Shown are the VWF expression levels as determined by ELISA and normalized to cell counts.
Figure 2D:
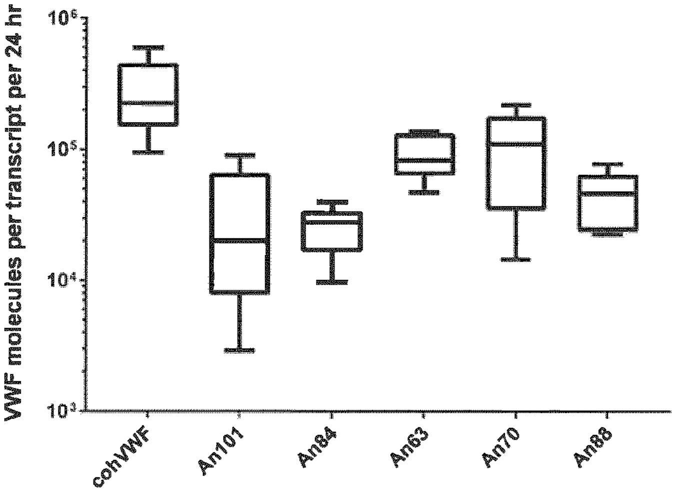
FIG. 2D shows biosynthetic efficiency of An-VWF protein production normalized to mRNA transcript levels. At the time of VWF protein determination by ELISA, mRNA was collected and RT-PCR was conducted compared to a plasmid standard curve.
Figure 3A:
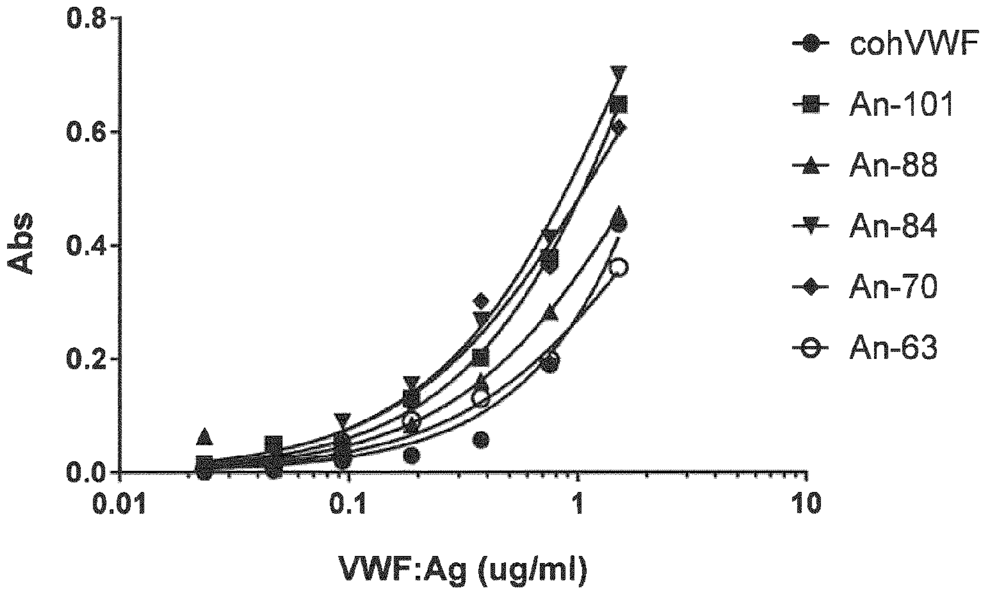
FIG. 3A shows a plot of absorbance (492 nm) versus VWF antigen (Ag) measured by ELISA. Capture of An-VWF proteins by human Factor VIII (Eloctate) was detected by anti-VWF antibodies.
Figure 3B:
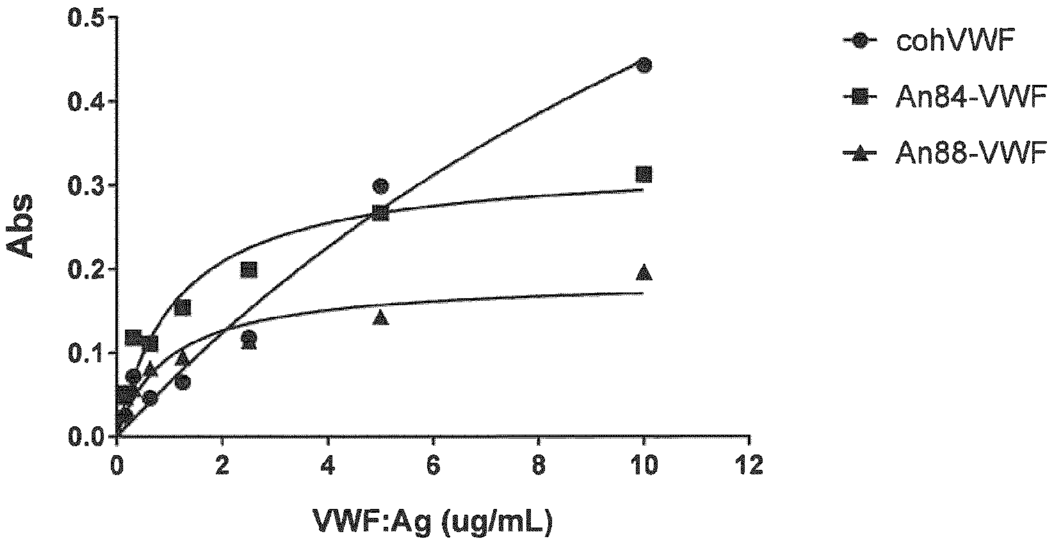
FIG. 3B shows a plot of absorbance (492 nm) versus VWF antigen (Ag) measured by ELISA. Human Factor VIII (Advate) was adsorbed to the plate and capture of An-VWF proteins was detected by anti-VWF antibodies.
Figure 3C:
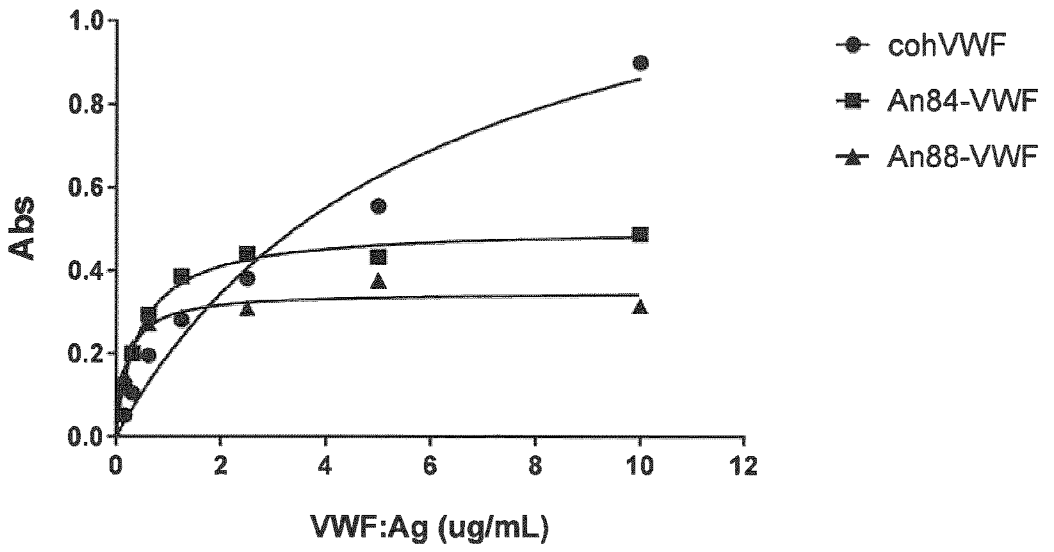
FIG. 3C shows a plot of absorbance (492 nm) versus VWF antigen (Ag) measured by ELISA. An-Factor VIII (An84-FVIII, SEQ ID No. 67) was adsorbed to the ELISA plate and capture of An-VWF proteins was detected by anti-VWF antibodies.
Figure 3D:
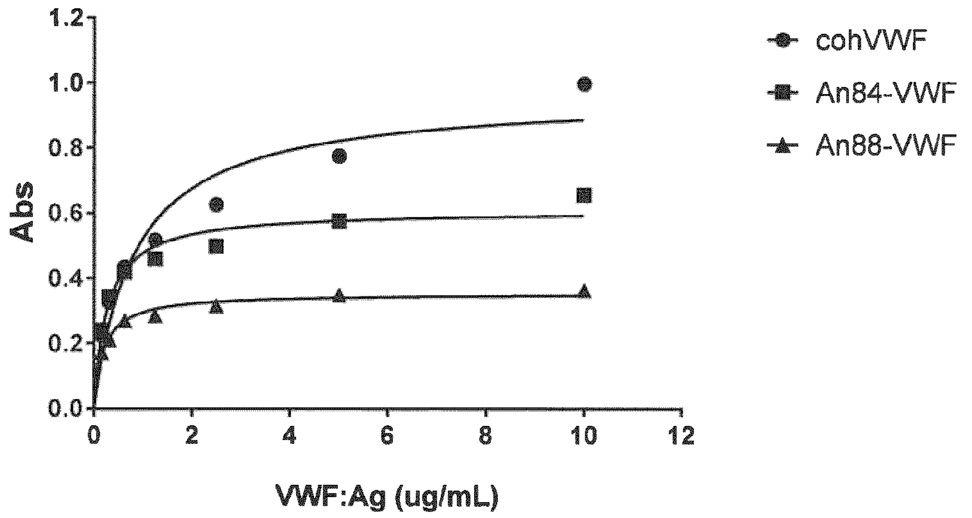
FIG. 3D shows a plot of absorbance (492 nm) versus VWF antigen (Ag) measured by ELISA. An-Factor VIII (An88-FVIII, SEQ ID No. 69) was adsorbed to the ELISA plate and capture of An-VWF proteins was detected by anti-VWF antibodies.
Figure 3E:
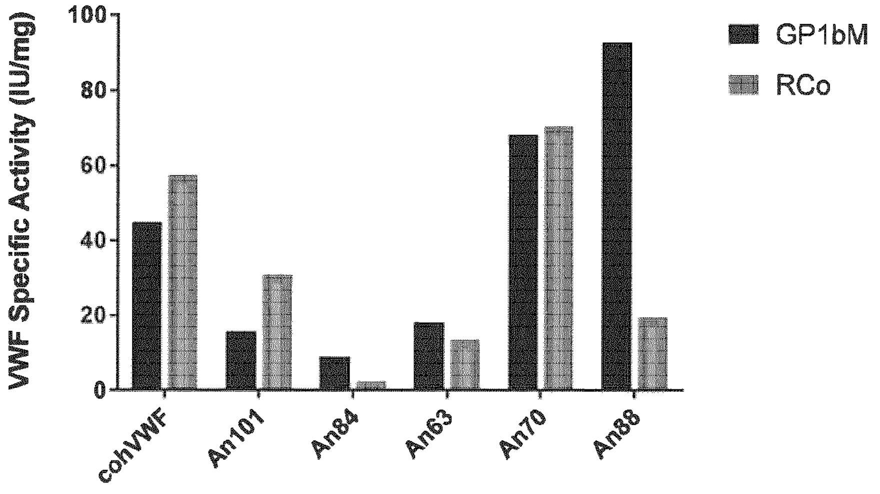
FIG. 3E shows specific activities of An-VWF proteins compared to recombinant human VWF as determined by ristocetin cofactor assay and GPIb-M assay. Specific activity was calculated as functional activity per unit mass.

Utilizing cell lines commonly employed in heterologous recombinant production, the biosynthetic production of VWF was investigated. Transient transfection of HEK116 and HEK293T cells demonstrated equivalent production of all An-VWF compared to the codon optimized human (coh) VWF (FIG. 2A) with the exception of An70 (SEQ ID No. 9) and An88-VWF (SEQ ID No. 7) (P=0.0284 and 0.0003, respectively for 116 cells; One Way ANOVA and P=0.0024 for An88-VWF (SEQ ID No. 7) in 293T cells). Additionally, there was no significant difference in VWF production between wildtype human VWF and the engineered cohVWF sequences in either HEK116 or HEK291T cell lines (P=0.8506 and 0.8372, respectively). Analysis of stable monoclonal cell lines, however, revealed no significant difference in VWF production despite lower median values (FIG. 2B; Dunn's One-Way ANOVA).

Immunohistochemistry of An-VWF was employed to visualize the cellular formation of pseudo-Weibel-Palade bodies (pWPBs) in HEK293 cells. Stable polyclonal populations expressing AnVWF all revealed the presence of pWPBs suggesting conserved tail-to-tail dimerization and head-to-head multimerization of VWF throughout mammalian evolution. Analysis of multimer formation in purified recombinant VWF by agarose gel electrophoresis confirmed the presence of high molecular weight multimers equivalent to cohVWF and plasma derived human VWF. These data demonstrate recombinant VWF has full multimeric potential when absent ADAMTS13. Recombinant An-VWF contains a population of ultralarge VWF multimers that were absent in human plasma. Additionally, the triplet bands seen in human plasma were not visible in An-VWF multimers.

In addition to serving as a chaperone for FVIII, VWF activated the GPIb/IX/V complex on platelets by binding through the VWF A1 domain (see VWF domains in Springer, T. A., Blood (2014), 124: 1412-1425). To first test the functional conservation of An-VWF molecules in a ristocetin-independent manner, AnVWF was assessed for GPIb binding via a GP1bM assay. In this assay, An70 (SEQ ID No. 9) and An88 (SEQ ID No. 7) displayed 1.5-2-fold increased specific activity over cohVWF (FIG. 3). VWF molecules An101 (SEQ ID No. 6), An84 (SEQ ID No. 8), and An63-VWF (SEQ ID No. 10) demonstrated conserved but reduced platelet activation function. These differences in activity are likely due to amino acid substitutions within the A1-domain, however, there are only 5 amino acid differences in the A1 domain of An101-VWF (SEQ ID No. 6) (see Table 3). Aggregation of washed normal human platelets in the presence of ristocetin (that binds to the VWF A1 domain and results in a permissive configuration) via the VWF:RCo assay resulted in similar specific-activities to GPIb-M determinations with the exception of An88-VWF (SEQ ID No. 7).

Figure 4A:
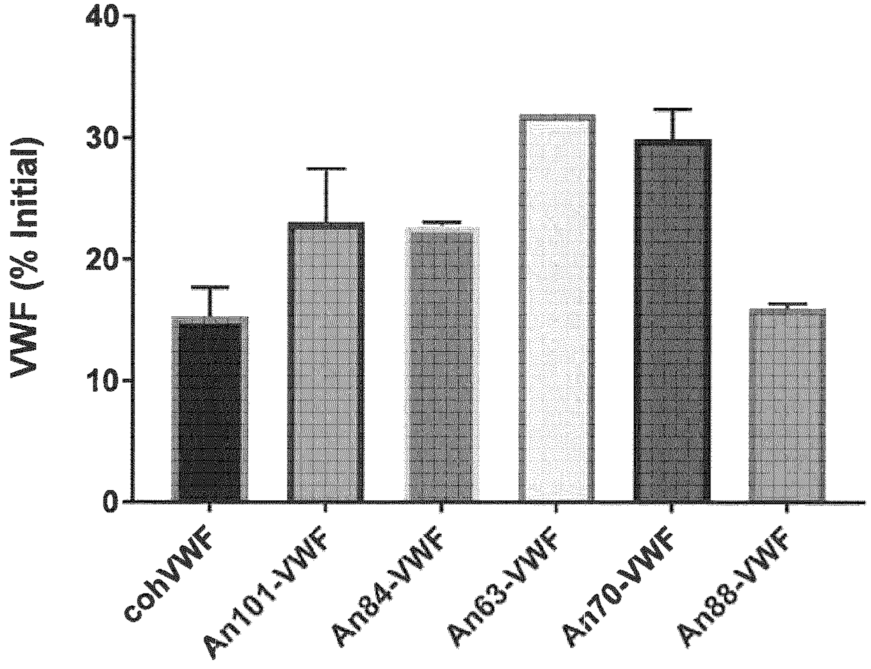
FIG. 4A shows a bar graph of residual An-VWF levels in mouse plasma after 1 h compared to human VWF. Notably, An-63 mouse received 10 μg due to low protein availability.
Figure 4B:
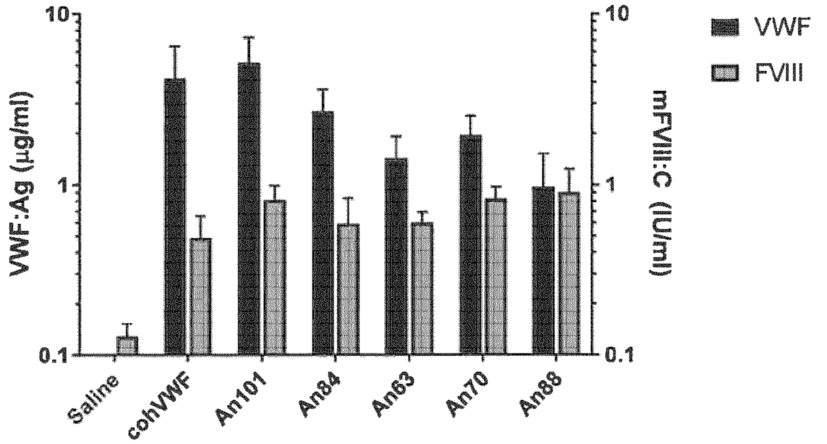
FIG. 4B shows in vivo rescue of FVIII levels in VWF deficient mice following hydrodynamic injection of An-VWF plasmid. VWF antigen levels were determined via ELISA and FVIII activities were determined by chromogenic assay from mouse plasma.

To determine if liver derived AnVWF can restore circulating levels of endogenous mouse FVIII in vivo, linear plasmid DNA containing AnVWF sequences were hydrodynamically injected into VWF deficient mice. Antigen levels were determined by ELISA and ranged from 10 to 52% normal levels (FIG. 4). Production of An63-VWF (SEQ ID No. 10) and An88-VWF (SEQ ID No. 7) were significantly lower than cohVWF (SEQ ID No. 11) production (P=0.0357 and 0.013; Dunnett's ANOVA). Endogenous mouse FVIII (mFVIII) activity levels were subsequently increased from 13% in VWF deficient mice receiving saline, to a range of 49-90% normal as determined by chromogenic assay. Mice injected with An88-VWF (SEQ ID No. 7) plasmid had significantly increased rescue of mFVIII despite significantly lower VWF concentrations (P=0.0412; Dunnett's ANOVA).

Figure 5A:
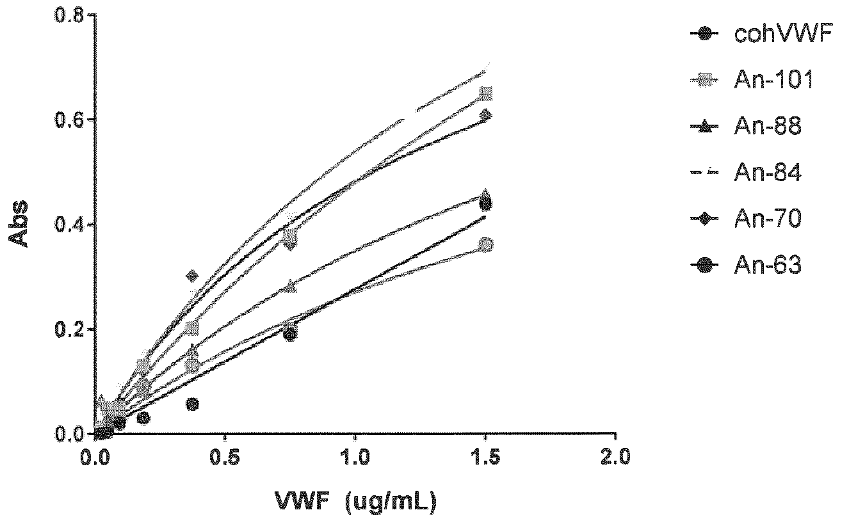
FIG. 5A shows a plot of absorbance (492 nm) versus VWF antigen (Ag) measured by ELISA capture of An-VWF proteins by adsorbed human Factor VIII (Eloctate).
Figure 5B:
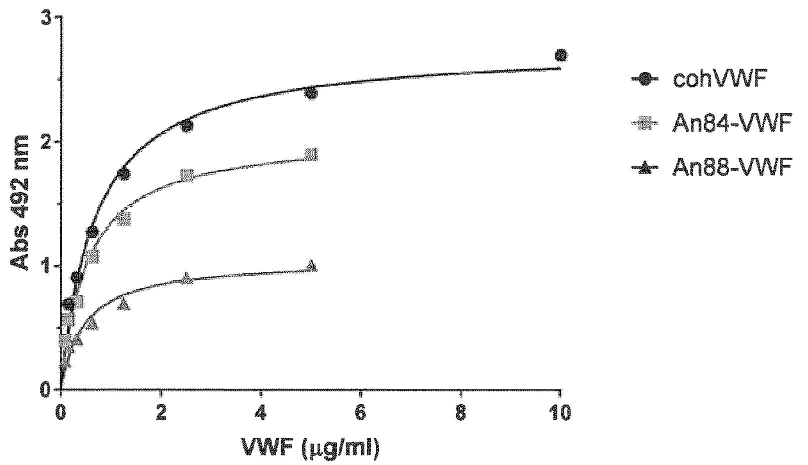
FIG. 5B shows a plot of absorbance (492 nm) versus VWF antigen (Ag) measured by ELISA capture of An-VWF proteins by adsorbed human Factor VIII (Advate).
Figure 5C:
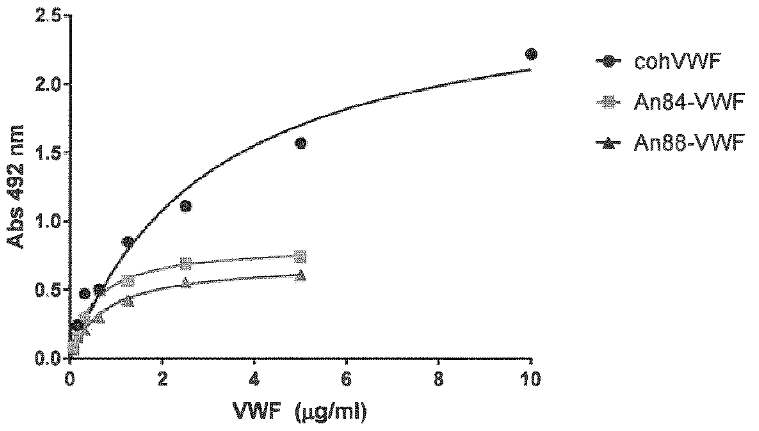
FIG. 5C shows a plot of absorbance (492 nm) versus VWF antigen (Ag) measured by ELISA capture of An-VWF proteins by adsorbed An-Factor VIII (An84-FVIII, SEQ ID No. 67)
Figure 5D:
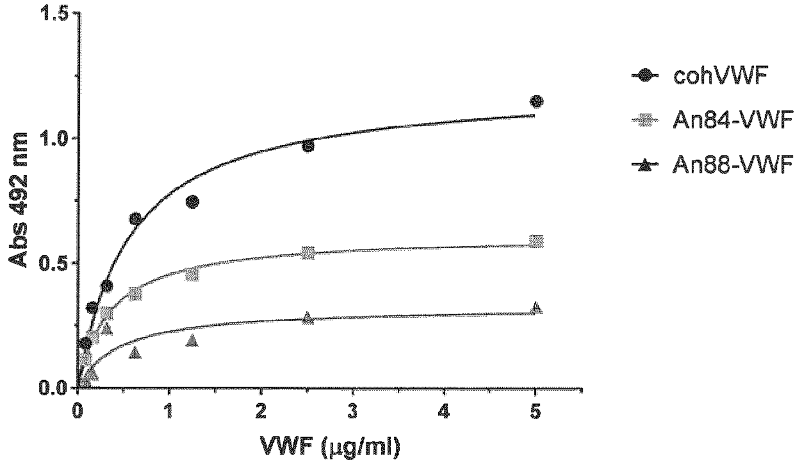
FIG. 5D shows a plot of absorbance (492 nm) versus VWF antigen (Ag) measured by ELISA capture of An-VWF proteins by adsorbed An-Factor VIII (An88-FVIII, SEQ ID No. 69)

The sub-nanomolar, strong affinity of FVIII for VWF protects it from rapid clearance, proteolytic deactivation, and this association is increasingly considered as immunoprotective. To test the ability of AnVWF to bind several FVIII molecules, ELISA-based binding analyses were performed. Human FVIII (Eloctate) demonstrated binding to all AnVWF molecules tested (FIG. 5A). Compared to human VWF, An84-VWF (SEQ ID No. 8) and An88-VWF (SEQ ID No. 7) demonstrated similar but improved (16.8 and 19.7-fold lower) $K_{dapp}$ values for human FVIII (Advate; FIG. 5B). An84-FVIII (previously reported as An53-FVIII in Zakas et al., *Nature Biotech.* 2017, 35: 35-37 and International Patent Application Publication No. WO 2016/123200, both hereby incorporated by reference in their entirety), a molecule with 95% identity to human FVIII, bound An84-VWF (SEQ ID No. 8) and An88-VWF (SEQ ID No. 7) with 5.8 and 4.2-fold improved $K_{dapp}$ values, respectively, compared to human VWF (see FIG. 5C). Conversely, An88-FVIII, (SEQ ID No.) demonstrated similar $K_{dapp}$ values for An84-VWF (SEQ ID No. 3) and An88-VWF (SEQ ID No. 7) compared to human VWF, respectively (FIG. 5D). This observation is likely due to the increased affinity of human VWF for An68-FVIII, revealing a 75-fold decrease in $K_d$ compared to human FVIII. Interestingly, An88-VWF (SEQ ID No. 7) displayed the lowest $K_d$ values across all FVIIIs tested.

Figure 6:
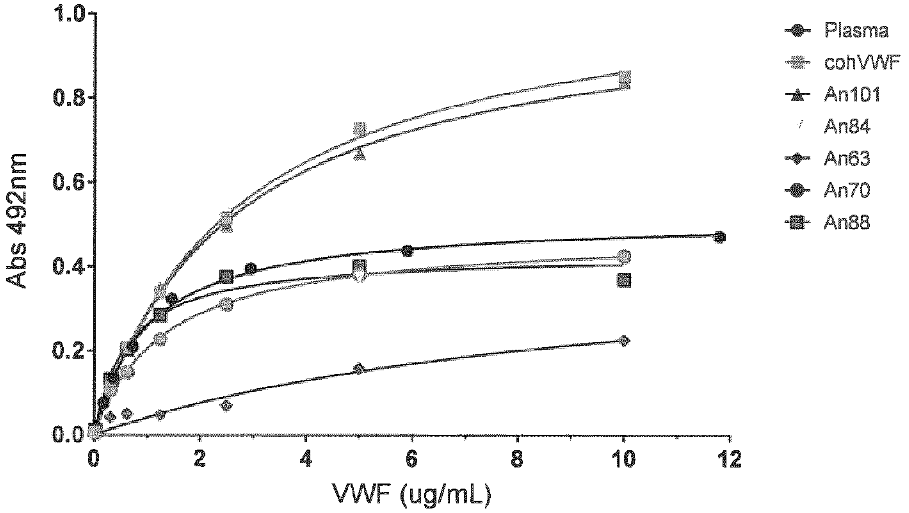
FIG. 6 shows absorbance (492 nm) versus VWF antigen (Ag) measured by ELISA capture of An-VWF proteins by human recombinant collagen.
Figure 7:
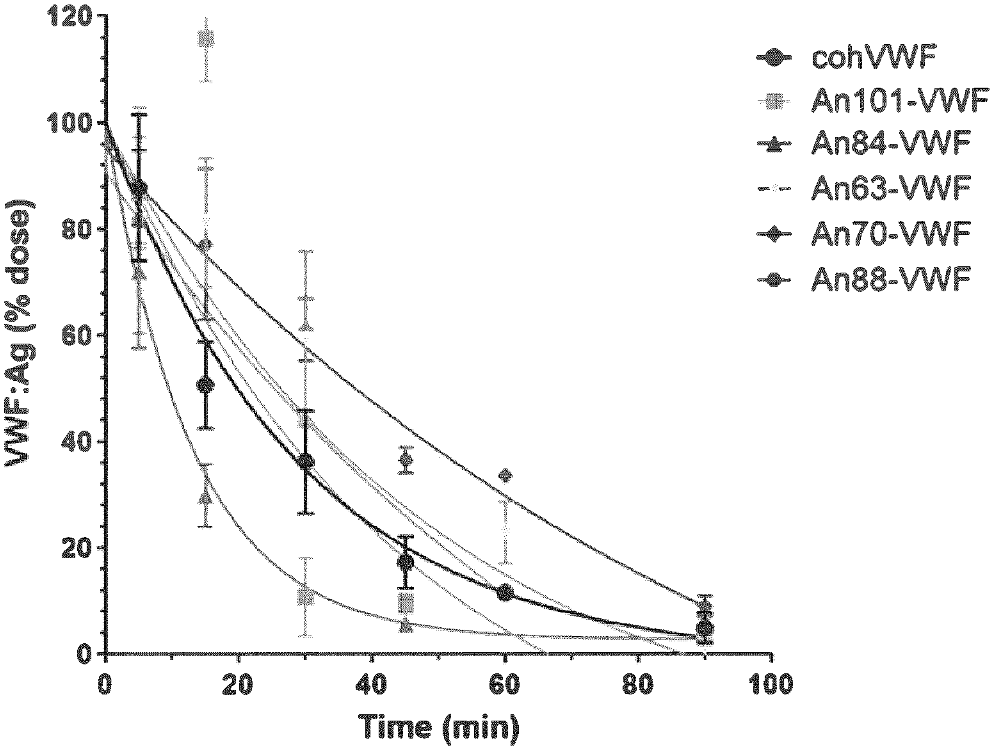
FIG. 7 shows in vivo clearance curves of An-VWF levels in mouse plasma following intravenous injection compared to human VWF. VWF antigen is determined by ELISA and normalized to the dose injected.

Exposure of collagen, primarily types I and III, in endothelial cells serves as a binding substrate for high molecular weight VWF to initiate platelet plug formation. As it has been hypothesized that shear forces and vasculature complexity have been significantly increased throughout evolution, we employed a collagen binding ELISA to test An-VWF association to human collagen. All An-VWF molecules demonstrated binding to human collagen (FIG. 6). Of note, An63-VWF (SEQ ID No. 10), demonstrated the lowest binding affinity to human collagen, roughly 3.5-fold lower than recombinant human VWF. An101-VWF (SEQ ID No. 6), however, demonstrated equivalent binding affinity to human VWF. This data suggests that VWF's ability to bind collagen type I through the A3 domain may have been a product of evolution as the earliest characterized VWF protein from hagfish lacked the A3 domain altogether. In rodent and ungulate lineage, An88-VWF (SEQ ID No. 7) and An70-VWF (SEQ ID No. 9) demonstrated a 4.3 and 2.1-fold increased affinity for human collagen, respectively.

To determine if liver derived AnVWF can restore circulating levels of FVIII in vivo, linear plasmid DNA containing AnVWF sequences were hydrodynamically injected into VWF deficient mice. At 24 hours post injection, peak VWF levels were detected from all AnVWF sequences and antigen levels ranged from 7 to 53% normal levels (Table 2). Interestingly, the relative levels of in vivo VWF biosynthesis mirror the production in transient transfection in HEK cells (compare Table 2 to FIG. 2A). Mouse FVIII (mFVIII) activity levels were subsequently increased from 13% in VWF deficient mice to a range of 42-75% normal. At these non-saturating VWF concentrations, molar ratios of VWF:FVIII demonstrate a 49:1 cohVWF:mFVIII ratio, near identical to the 50:1 ration observed in human plasma. Furthermore, these molar ratios approach equimolar concentrations as the VWF molecule increases identity to mouse VWF, resulting in a 6:1 ratio on An88-VWF (SEQ ID No. 7): mFVIII, providing support for a co-evolution hypothesis.

VWF is a complex, multifunctional scaffold protein within the hemostatic system. In addition to serving as a chaperone for FVIII, VWF activates the platelets GP1b complex by binding through the VWF A1 domain. To test the functional conservation of the An-VWF molecules in a ristocetin-independent manner, AnVWF was assessed for platelet activation via GP1bM assay. An-VWFs, specifically, An101 (SEQ ID No. 6), An84 (SEQ ID No. 8), and An63 (SEQ ID No. 10) retained platelet activation function albeit at a reduced specific activity compared to the cohVWF (SEQ ID No. 11) molecule (Table 3). The two VWF molecules representing the ungulate and rodent lineages, An70 (SEQ ID No. 9) and An88 (SEQ ID No. 7), respectively, conversely displayed 1.5-2-fold increased specific activity. These differences are likely due to amino acid substitutions at residues known to be associated with VWD type 2B and 2M gain- and loss-of-function mutations, respectively. The variable activation of human GP1b by AnVWF within primate evolution suggests that VWF and the GP1b complex either co-evolved with incompatibilities between reconstructed and modern proteins, or that evolutionary pressures favored diminished platelet activation to mitigate thrombotic effects. Considering that venous thrombotic effects are almost exclusive within humans, and considering that FVIII molecular evolution suggests thrombosis exhibited greater selection pressure, the hypothesis of co-evolution resulting in incompatible VWF-GP1b interactions is congruent.

The half-life of VWF is largely mitigated by LRP1, ASGPR, CLEC4M, and Stabilin-2 receptors. Because VWF is a molecular chaperone for FVIII, the half-life of FVIII is almost entirely dependent on VWF pharmacokinetics. As a result, current generation FVIII therapeutics using fusion proteins or post-translational modifications to FVIII alone have demonstrated only moderate extensions of half-life.

Conversely, a VWF molecule with an extended half-life would significantly increase the FVIII half-life so long as the affinity of FVIII for the exogenous VWF molecule is greater than that of endogenous VWF. Therefore, a suitable engineered VWF fragment provided in combination with a FVIII protein as a singular therapeutic (i.e., complex) would represent a novel and advantageous product. To identify potential VWF fragment molecules for this purpose, clearance rates of recombinant AnVWF were measured, in addition to FVIII affinity studies described above, compared to the cohVWF molecule. Briefly, 20 μg of protein was injected intravenously into male VWF deficient mice and assessed VWF concentrations at 5 and 60 minutes. Analysis revealed that An63-VWF (SEQ ID No. 10), An70-VWF (SEQ ID No. 9), An88-VWF (SEQ ID No. 7) and An101-VWF (SEQ ID No. 6) retained increased levels of VWF in circulation at 30 and 60 minutes post infusion. Specifically, 32.0 and 29.9% residual antigen compared to 15.3% cohVWF (SEQ ID No. 11) (FIG. 4; P=0.0044 and 0.0024, One Way ANOVA; n=1 and 3, respectively). Since An88-VWF (SEQ ID No. 7)-VWF also demonstrated increased affinity for human FVIII compared to human VWF, this molecule was identified as a candidate for a FVIII-VWF complex or combination product.

Heterologous expression in HEK293 cells demonstrated that all An-VWF sequences resulted in secreted antigen as determined by ELISA using anti-human VWF polyclonal antibodies. Furthermore, immunohistochemistry of HEK293 cells expressing An-VWF revealed the formation of pseudo Weibel-Palade bodies by all VWF proteins. Stably transected, clonal producer cell lines were generated and utilized for recombinant VWF production and purification using heparin-sepharose affinity chromatography. Consistent with our IHC studies, multimer analysis of the purified proteins revealed the presence of high molecular weight multimers equivalent to human plasma VWF. To test the functionality of An-VWF, the VWF:GPIbM assay was performed. Compared to an observed specific activity of 45 IU/mg VWF for cohVWF, An-VWF molecules displayed specific activities ranging from 6 to 94 IU/mg (see Table 3). These data suggest that VWF and GPIb may have co-evolved to regulate platelet adhesion and activation. Hydrodynamic injection of An63-VWF (SEQ ID No. 10), An88-VWF (SEQ ID No. 7), and An101-VWF (SEQ ID No. 6) plasmid DNA into VWF deficient mice revealed plasma VWF levels of 1.44±0.48, 0.72±0.16, and 2.9 μg/mL at 24 hours after administration, respectively (n=4, 3, and 1). Additionally, endogenous mouse (m) FVIII levels in these mice were elevated to 61±9, 75±16, and 67% of normal levels from a basal 12.9±2.4%. This data demonstrates that liver synthesized An-VWF retains FVIII association and stabilization. Molar ratios of An88-VWF (SEQ ID No. 7):mFVIII are 6:1 compared to 14:1 and 25:1 for An63-VWF (SEQ ID No. 10) and An101-VWF (SEQ ID No. 6), respectively, supporting the coevolution hypothesis for VWF and FVIII. Cumulatively, this study further validates the utility of SR for the generation of functional sequences for complex proteins with a high propensity for inactivating mutations. Further analysis of such sequences may provide greater resolution of amino acid sequences responsible for biochemical properties including clearance and FVIII association.

A combination of An-FVIII (e.g., SEQ ID Nos. 66 to 69) with An-VWF (e.g., SEQ ID Nos. 6 to 10, 12 to 63) was designed to improve the pharmacokinetic profile, potency, and efficacy of FVIII protein. Such a combination could be a complex that is, for example, co-expressed but isolated as the complex, or made into a complex and delivered in a single dose such as, for example, a single injection. Thus, gene therapy with co-administration of a pharmacological agent as described herein may provide a synergistic approach to treatment of bleeding disorders.

This improved combination product (e.g., complex) is likely to demonstrate prolonged half-life in the plasma due to reduced clearance. The target patient population for this combination product or complex includes all hemophilia A patients, both congenital and acquired, as well as a subset of VWD patients. VWD patients with mutations that disrupt the association between VWF and FVIII (Type 2N) have low FVIII in circulation. Therefore, this population would benefit greatly from this combination product or complex. Additionally, type III VWD patients have little to no detectable VWF and would also benefit factor replacement product. Finally, VWD type I patients who are undergoing surgeries or experiencing significant trauma and need additional hemostatic coverage would also benefit from this FVIII-replacement product.

A complex of An-FVIII with An-VWF was designed to improve the pharmacokinetic profile, potency, and efficacy of the FVIII protein. An-FVIII has demonstrated increased specific-activity and stability in its activated form, therefore less protein to be infused. The described complexes will result in a prolonged half-life of FVIII in the plasma due to the reduced clearance of the exogenous VWF chaperone protein. Additionally, the increased affinity of an An-FVIII molecule for An-VWF mitigates competition of the exogenous FVIII with endogenous VWF. Therefore, the clearance of FVIII is mediated by the reduced clearance of the exogenous VWF instead of the more rapid clearance of endogenous VWF. Providing the An-FVIII and An-VWF together in complex prevents rapid degradation and clearance of FVIII prior to association with VWF. Hence such a complex would provide a better FVIII because of specific activity/stability, and better half-life of FVIII because the VWF is improved. Gene therapy with co-administration of a pharmacological agent as described herein may provide a synergistic approach to treatment of bleeding disorders.

In certain embodiments, the disclosure contemplates pharmaceutical compositions comprising a recombinant or chimeric VWF protein and a pharmaceutically acceptable excipient. In certain embodiments, the disclosure contemplates methods of inducing blood clotting comprising administering an effective amount of a pharmaceutical composition disclosed herein to a subject in need thereof. In certain embodiments, the subject is at risk for, suspected of, exhibiting symptoms of, or diagnosed with a blood clotting disorder, e.g., wherein the subject is diagnosed with hemophilia A or acquired hemophilia.

In certain embodiments, the disclosure contemplates method of inducing blood clotting comprising administering an effective amount of a pharmaceutical composition comprising a vector encoding a protein disclosed herein to a subject in need thereof wherein the subject is diagnosed with hemophilia A or acquired hemophilia under conditions such that the protein is expressed inducing blood clotting. In certain embodiments, the subject is unlikely to respond to exogenous FVIII infusions.

In certain embodiments, the disclosure relates to expression systems comprising nucleic acids or vectors comprising nucleic acids disclosed herein. The selected vector may be delivered by any suitable method, including intravenous injection, ex-vivo transduction, transfection, electroporation, liposome delivery, membrane fusion techniques, high velocity DNA-coated pellets, viral infection and protoplast fusion. CpG DNA motifs are typically removed because they may lead to gene methylation and silencing. See Bird, DNA methylation and the frequency of CpG in animal DNA, 1980*, Nucleic Acids Res,* 8: 1499-1504. CpG removal also helps the vector evade immune detection, enhancing the safety and efficacy of the vector. See *J Clin Invest.* 2013, 123(7): 2994-3001, entitled "CpG-depleted adeno-associated virus vectors evade immune detection."

In certain embodiments, the disclosure relates to methods of treating a subject diagnosed with a genetic trait that results in expression of a mutated or truncated non-functional protein by administering an effective amount of a vector disclosed herein. In certain embodiments, the vector is configured to express a functional protein from the liver. In certain embodiments, the vector is configured to express a protein in any cells such as hematopoietic stem cells or other hematocytes in vivo or by ex vivo transduction.

Adeno-associated virus, Parvovirus family, is an icosahedral virus with single-stranded linear DNA genomes. The life cycle of adeno-associated virus includes a latent phase at which adeno-associated virus genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make adeno-associated virus an attractive tool for gene transfer.

In certain embodiments, this disclosure provides for a nucleic acids disclosed herein the encoded proteins or wherein the nucleic acids are part of an expression cassette or transgene. See e.g., US Pat. App. Pub. 20150139953. In certain embodiments, the expression cassette is composed of a transgene and regulatory sequences, e.g., promotor and 5' and 3' AAV inverted terminal repeats (ITRs). In one desirable embodiment, the ITRs of AAV serotype 2 or 8 are used. However, ITRs from other suitable serotypes may be selected. An expression cassette is typically packaged into a capsid protein and delivered to a selected host cell.

Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously added factors, for example.

Introduction of the molecules (as plasmids or viruses) into the host cell may be accomplished using techniques known to the skilled artisan. In preferred embodiment, standard transfection techniques are used, e.g., CaPO.sub.4 transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

Recombinant or chimeric proteins and virus particles, capsids, or vectors encoding proteins disclosed herein can be delivered, e.g., to liver via the hepatic artery, the portal vein, or intravenously to yield therapeutic levels of therapeutic proteins or clotting factors in the blood. The recombinant or chimeric proteins and capsid or vector is preferably suspended in a physiologically compatible carrier, may be administered to a patient. Suitable carriers may be readily selected by one of skill in the art in view of the indication. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, sesame oil, and water.

Optionally, compositions of the disclosure may contain other pharmaceutically acceptable excipients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin. Recombinant virus particles, capsids, or vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the liver (optionally via the hepatic artery) or lung), oral, inhalation, intranasal, intratracheal, intraarterial, intraocular, intravenous, intramuscular, subcutaneous, intradermal, and other parental routes of administration. Routes of administration may be combined, if desired.

Dosages of the recombinant or chimeric proteins and virus particles, capsids, or vectors will depend primarily on factors such as the condition being treated, the age, weight and health of the patient, and may thus vary among patients. For example, a therapeutically effective human dosage of the protein is generally in the range of from about 0.1 ml to about 100 ml of solution containing concentrations of from about 1.times.10.sup.9 to 1.times.10.sup.16 genomes, virus vectors, or gene modified cells produced by ex vivo transduction.

As used herein, a therapeutically effective amount is an amount of protein or vector that produces sufficient amounts of VWF to decrease the time it takes for the blood of a subject to clot. For example, severe hemophiliacs have a whole blood clotting time of greater than 60 minutes as compared to approximately 10 minutes for non-hemophiliacs.

In the following descriptions of various embodiments of An-VWF proteins or nucleic acids, references to sequences and sequence listings are made. Those of ordinary skill in the art will readily appreciate that the invention is not limited to the specific sequences described, as many variants are possible without departing from the invention. For example, substitutions, mutations, deletions, and/or additions of one or more nucleotides or amino acids may be made, or may occur, without substantial effect on functional properties of the An-VWF proteins or nucleic acids. Such a functional equivalent may have, for example, 60%, or 70%, or 80%, or 90%, or more sequence identity with a sequence described herein. Such functional equivalents are intended to be included in the embodiments of the invention.

The following working examples further illustrate the present invention and are not intended to be limiting in any respect.

Working Examples

Materials

DMEM and Opti-MEM cell culture media, HBSS, and Geneticin were purchased from Gibco Life Technologies (Waltham MA). Fetal Bovine serum was purchased from VWR (Radner, PA). Cell culture plates, flasks, and ELISA costar 96-well plates were purchase from Corning (Corning, NY) and conical tubes were purchased from Sarstedt (Nümbrecht, Germany). Restriction enzymes NheI, AgeI, NotI, and BssHII were purchased from New England Biolabs (Ipswich, MA). Heparin-Sepharose 6 Fast Flow was purchased from GE Healthcare (Chicago, IL) and Poly-Prep columns were purchased from Bio-Rad (Hercules, CA). HEK cell lines were purchased from ATCC (Manassas, VA). Polyethylenimine, o-phenylenediamine dihydrochloride, RNAlater, bovine serum albumin, and M2 anti-FLAG antibody were purchased from Sigma-Aldrich (St. Louis, MO). DNA and RNA purification kits were purchased from Qiagen (Germantown, MD) and Omega Bio-Tek (Norcross, GA). Amicon 50K NMWL filters were purchased from EMD Millipore (Burlington, MA) Immunohistochemistry DAKO protein block, DAKO mounting medium, isotype antibody X0936, polyclonal rabbit anti-human VWF antibodies A0082 and P0226 were purchased from Agilent (Santa Clara, CA). Factor VIII chromogenic SP4 assay was purchased from Diapharma (Chester, OH). WHO standard human plasma, and the INNOVANCE VWF:Ac kit were purchased from Siemens (Munich, Germany). RNase Inhibitor RiboLock, Power SYBR™ Green PCR master mix, and Multiscribe™ reverse transcriptase were purchased from Thermo Fisher Scientific (Waltham, MA). Human collagen type I was purchased from StemCell Technologies (Vancouver, Canada) and human collagen type III was purchased from Sigma-Aldrich (St. Louis, MO). Maleic anhydride activated plates were purchased from Thermo Scientific (Waltham, MA).

Example 1. An-VWF Sequence Inference

An-FVIII sequence reconstruction was performed as described previously 18, 19. Briefly, 59 mammalian FVIII sequences were aligned using MUSCLE and an evolutionary tree was inferred using MrBayes. Sequences were inferred using both DNA and amino acid-based models in PAML VERSION 4.1. The multiple sequence alignment is electronically available upon request.

Example 2. An-VWF DNA Synthesis

Amino acid sequences for human An-VWF (hVWF), An101 (SEQ ID No. 6), An88 (SEQ ID No. 7), An84 (SEQ ID No. 8), An70 (SEQ ID No. 9), and An63 (SEQ ID No. 10)

were codon optimized (co) for human host expression and synthesized by GenScript (Piscataway, N.J.). Coding DNA sequence was flanked by 5' NheI and AgeI restriction sites and 3' NotI sites for subcloning into the mammalian expression vector pCI-Neo. Additionally, a C-terminal glycine hinge (GGRGG (SEQ ID NO:70)), TEV protease motif (ENLYFQG (SEQ ID NO:71)), and 3×FLAG tag (DYKDDDDKDYKDDDDKDYKDDDDK (SEQ ID NO:72)) with the nucleic acid sequence, GGCGGCAGAGGAGGAGAGAACCTGTACTTCCAGGGCGACTATAAGGAC GATGACGATAAGGATTACAAAGATGATGACGATAAGGATTATAAAGACGATGACGA TAAGTGA (SEQ ID NO:73), were added to each sequence for detection, purification, and subsequent removal following purification.

Example 3. Cell Lines

The current study utilized several cell variants of human embryonic kidney (HEK) cells maintained in DMEM with 10% FBS. Transient transfections were performed in HEK293T and HEK116 cells, and polyclonal stable cell lines were generated in HEK293 cells. Stable monoclonal producer cell lines were generated from HEK116 cells due to increased protein biosynthesis.

Example 4. ELISA

Detection of AnVWF antigen was performed by sandwich ELISA using DAKO polyclonal rabbit anti-human VWF antibodies A0082 and P0226 at 1:1000 dilutions in PBS or blocking buffer, respectively. Absorbance of o-phenylenediamine turnover by horseradish peroxidase was determined by absorbance at 492 nm following addition of 1M H2SO4. Absorbance was interpolated to a standard curve generated with WHO defined human standard plasma. VWF samples were diluted in PBS to ensure sufficient excess of polyclonal antibodies. For FVIII binding assays, FVIII was diluted to 1.5 μg/ml (Advate diluted to 2.4 μg/ml) in 20 mM bicine 2 mM CaCl2 at pH 9.0 and adsorbed to ELISA plate. Dilutions of AnVWF in HEPES buffered saline (HBS; 20 mM HEPES, 150 mM NaCl) were captured and detected using DAKO P0226 with o-phenylenediamine after sulfuric acid quench. Absorbance was interpolated to a standard curve generated with WHO defined human standard plasma.

Example 5. An-VWF Expression and Purification

Transient transfections were conducted using 0.5 μg plasmid DNA with 0.5 μg PEI per 105 cells in serum-free DMEM without antibiotic. Media was exchanged 24 hours after transfection and VWF production was determined after an additional 24 hours. Antibiotic selection of stable producers was conducted using 500 μg/ml geneticin in 10 cm plates. At 24 hours post media exchange, cell counts, RNAlater™ collections, and VWF determinations were performed simultaneously. Highest producing cell lines were expanded into triple flasks for protein production and purification from serum-free OptiMEM media. Conditioned supernatant was separated from cellular debris by centrifugation at 300 rcf for 15 mM and 0.45 μm filtration. Filtered collections were stored at −20° C. with 0.05% sodium azide until purification. AnVWF collections were diluted 1:1 with 20 mM HEPES, 5 mM CaCl2, 0.01% Tween-80 pH 7.2 prior to purification. Purification of AnVWF was performed by heparin-sepharose affinity chromatography at a flowrate of 1-2 ml/min. Column was equilibrated and washed with 20 mM HEPES, 5 mM CaCl2, 50 mM NaCl, 0.01% Tween-80 at pH 7.2. AnVWF was eluted with 650 mM NaCl and manually fractionated. Fractions containing VWF by ELISA were pooled and centrifuge concentrated in Amicon 50K NMWL filters and stored at 4° C. Following 48-72 hours at 4° C., AnVWF was centrifuged at 12,000 rcf for 10 minutes to separate fibronectin precipitate. VWF containing supernatant was aliquoted and stored at −80° C. Final concentrations of AnVWF were determined by ELISA.

Example 6. RNA Isolation and RT-PCR

Monoclonal cell lines stably producing AnVWF were centrifuged at 300 rcf for 10 minutes, washed with HBSS, and centrifuged again. Pellets were re-suspended in 300 μL RNAlater and stored at −80° C. until RNA isolation. RNA was purified using Qiagen RNeasy product according to manufacturer's protocol. RNA was stored at −80 C until analysis by RT-PCR. Transcript analysis was conducted as previously described 14. Briefly, universal VWF primers within the D3 domain (Forward 5'-GAGAACGGCTACGAGTGCG (SEQ ID NO:74), Reverse 5'-CTGGAGGACAGTGTGCGTG (SEQ ID NO:75)) were validated for all AnVWF plasmids. Transcript levels were determined from 50 ng RNA using one-step RT-PCR through interpolation to the cohVWF plasmid DNA standard curve. Total VWF transcripts per cell was calculated using a generic estimate of 25 μg RNA per HEK116 cell.

Example 7. Immunohistochemistry

Glass coverslips were coated with 10 μg/ml poly-L-lysine for 1 hour in 24-well plates. Coverslips were washed with HBSS and 2×105 polyclonal stable VWF-producer cells were seeded onto the coverslip. The following day cells were washed 3 times at 5 minutes with ice cold PBS and fixed for 20 min with BD fixative. Following 3 washes with PBS, cells were permeabilized with PBS containing 0.1% Triton X 100. Permeabilized cells were washed 3 times with PBS and blocked using DAKO protein block. Following an additional 3 washes in PBS, primary antibody DAKO A0082 or rabbit isotype control X0936 was diluted to 3 μg/ml in PBS with 1% BSA in the presence of 1 μg/ml Phalloidin TRITC (568) and applied to the cells overnight at 4° C. in dark conditions. Antibodies were washed 5 times with PBS and stained with 2.5 μg/ml P0226 in PBS with 1% BSA for 1 hour. Following 5 washes with PBS, cell nuclei were stained with DAPI at 1 μg/ml for 10 minutes, washed 3 final times, and mounted using DAKO mounting medium. Confocal images were taken by laser scanning microscope Leica TCS SP8 HyVolution 2 (Leica Microsystems, Concord, ON, CA)

Example 8. Multimer Analysis

Multimer analysis was performed as previously reported 20-22. Briefly, 60 ng of VWF was separated by a 1.4% SDS-agarose gel. Multimers were visualized by chemiluminescent-based imaging using a horseradish peroxidase conjugated polyclonal rabbit anti-human VWF antibody P0226 (Dako).

Example 9. ADAMTS13 Cleavage

An-VWF digestion using recombinant human ADAMTS13 was performed as previously described 23, 24.

Human ADAMTS13 was diluted 2-fold in 5 mM Tris (tris(hydroxymethyl) aminomethane), pH 8.0, and activated with 10 mM BaCl2 for 5 min at 37° C. 25 μL of diluted hADAMTS13 was added to 25 μL of An-VWF (1 U/mL in 1.5M urea, 5 mM Tris) and incubated for 24 h at 37° C. EDTA, at a final concentration of 50 mM, was added to stop the reaction. Multimer analysis was performed as described above.

Example 10. In Vivo an-FVIII Production and FVIII Rescue

All animal procedures were in accordance with the Canadian Council on Animal Care guidelines and approved by the Queen's University Animal Care Committee. AnVWF plasmid in the mammalian expression vector pCI-Neo was linearized using BssHII, column purified, and quality assessed by agarose gel electrophoresis. 10 μg of linear DNA was diluted in TransIT-EE hydrodynamic buffer (Minis) at a volume of 10% mouse body weight and injected into 8-12 week old VWF−/− females via tail vein within 5-8 seconds. VWF−/− mice are bred on a C56BL/6 background. Retro-orbital samples were collected at 24 hours post injection and plasma was analyzed for VWF concentration by ELISA and FVIII activity by chromogenic SP4 assay using a WHO human plasma as a standard. Molar concentrations of FVIII were determined using a specific activity of 4000 IU/mg for murine FVIII.

Example 11. Clearance

Clearance studies were performed in 8-12 week old male VWF −/− mice. Twenty μg of AnVWF was diluted in 0.9% saline and injected via tail vein. Retro orbital sampling was performed from alternate eyes at 5 minutes post injection and one additional time point. Plasma was stored at −80° C. prior to VWF determination by ELISA. Percent residual VWF was determined relative to the VWF concentration at 5 minutes.

Example 12. VWF:CP1bM and VWF:RCo Activity Assays

The Innovance VWF:Ac GP1bM assay was performed on a BCS-XP coagulometer (Siemens) according to manufacturer's instructions. Purified AnVWF was diluted in OVB buffer and compared to a standard curve of WHO defined human standard plasma. Specific activity was defined as the ratio of GP1bM activity to VWF antigen concentration in IU/mg. Activity by VWF:RCo was measured via platelet aggregometry using freshly prepared, washed normal platelets and compared to a WHO standard plasma, as previously described.

Example 13. Collagen Binding

Collagen binding assays were performed as previously reported 26, 27 using human collagen type I and III. Briefly, maleic anhydride activated plates were coated with 10 μg/ml human collagen (95% type I, 5% type III) for 2 hours at room temperature. Plate was washed three times with 75 mM NaCl, 5 mM Tris, 0.1% Tween-20, pH 9.1 and blocked overnight in phosphate buffered saline with 5% BSA. Recombinant AnVWF protein curves were diluted in PBS with 1% BSA, 0.1% Tween-20 and applied to collagen coated plate. VWF was detected with DAKO anti-human VWF polyclonal antibody P0226 at a dilution of 1:1000 in diluent. Absorbance of HRP mediated catalysis of OPD was conducted at 492 nm. An-VWF curves were compared to human recombinant VWF and reference human plasma was also included.

In Vivo An-FVIII Production and FVIII Rescue

VWF−/− mice on a C56BL/6 background were housed in accordance with Queen's University. AnVWF plasmid in the mammalian expression vector pCI-Neo was linearized using BssHII, column purified, and quality assessed by agarose gel electrophoresis. 10 μg of linear DNA was diluted in TransIT-EE hydrodynamic buffer (Mirus) at a volume of 10% mouse body weight and injected into 8-12 week old females via tail vein within 5-8 seconds. Retro-orbital samples were performed at 24 and 72 hours post injection and plasma was analyzed for VWF concentration by ELISA and FVIII activity by chromogenic SP4 assay. Clearance studies were performed in 8-12 week old male VWF −/− mice. Twenty μg of AnVWF was diluted in 0.9% saline and injected via tail vein. Retro orbital sampling was performed in alternate eyes at 5 and 60 minutes post injection. Plasma was assayed for VWF by ELISA and percent residual VWF was determined in proportion to the concentration at 5 minutes.

All cited publications are incorporated herein by reference in their entirety.

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

TABLE 1

An-VWF identity to human VWF

| VWF | Amino Acid Substitutions | % Human Identity | Predicted Age (mya) | Lineage |
|---|---|---|---|---|
| cohVWF SEQ ID No. 11 | 0 | 100 | — | Primate: Human |
| An101-VWF SEQ ID No. 6 | 81 | 97.1 | 43.2 | Primate: Simiiformes |
| An84-VWF SEQ ID No. 8 | 206 | 92.7 | 89.8 | Primate/Rodent: Euarchontoglires |
| An63-VWF SEQ ID No. 10 | 245 | 91.3 | 105.5 | Early Common Ancestor: Eutheria |
| An70-VWF SEQ ID No. 9 | 307 | 89.1 | 64.2 | Ungulate: Artiodactyla |
| An88-VWF SEQ ID No. 7 | 364 | 87.1 | 32.7 | Rodentia: Muroidea |

mya: million years ago

TABLE 2

Liver-derived An-VWF restores FVIII in mice

| | VWF:Ag (μg/ml) | FVIII:C (IU/ml) | n = | Molar Ratio (VWF:FVIII) |
|---|---|---|---|---|
| Saline | 0 | 0.129 ± 0.024 | 9 | NA |
| cohVWF SEQ ID No. 11 | 3.63 ± 2.29 | 0.42 ± 0.113 | 3 | 49:1 ± 18 |
| An101-VWF SEQ ID No. 6 | 5.29 ± 2.54 | 0.75 ± 0.112 | 3 | 41:1 ± 15 |

TABLE 2-continued

| Liver-derived An-VWF restores FVIII in mice | | | | |
|---|---|---|---|---|
| | VWF:Ag (μg/ml) | FVIII:C (IU/ml) | n = | Molar Ratio (VWF:FVIII) |
| An84-VWF SEQ ID No. 8 | 3.07 ± 1.18 | 0.58 ± 0.357 | 2 | 34:1 ± 9 |
| An63-VWF SEQ ID No. 10 | 1.44 ± 0.48 | 0.61 ± 0.09 | 4 | 14:1 ± 5 |
| An70-VWF SEQ ID No. 9 | 2.1 ± .305 | 0.76 ± .046 | 2 | 17:1 ± 1 |
| An88-VWF SEQ ID No. 7 | 0.72 ± 0.16 | 0.75 ± 0.16 | 3 | 6:1 ± 2 |

TABLE 3

| Identity of An-A1 domains compared to human | | | |
|---|---|---|---|
| VWF | A1 Domain Amino Acid Substitutions | % Human Identity | Specific Activity* (IU/mg) |
| cohVWF SEQ ID No. 11 | 0 | 100 | 44.8 |
| An101-VWF SEQ ID No. 6 | 5 | 98 | 11.4-19.9 |
| An84-VWF SEQ ID No. 8 | 21 | 90 | 6.3-11.7 |
| An63-VWF SEQ ID No. 10 | 26 | 88 | 13.9-22.5 |
| An70-VWF SEQ ID No. 9 | 32 | 85 | 50.1-86.3 |
| An88-VWF SEQ ID No. 7 | 28 | 87 | 91.4-94.4 |

*Specific Activity determined by VWF: GPIbM assay and ELISA

TABLE 4

| Correspondence between Sequence Names and SEQ ID Numbers | |
|---|---|
| Sequence Name | SEQ ID No. |
| An101-VWF DNA | SEQ ID No. 1 |
| An88-VWF DNA | SEQ ID No. 2 |
| An84-VWF DNA | SEQ ID No. 3 |
| An70-VWF DNA | SEQ ID No. 4 |
| An63-VWF DNA | SEQ ID No. 5 |
| An101-VWF Prot | SEQ ID No. 6 |
| An88-VWF Prot | SEQ ID No. 7 |
| An84-VWF Prot | SEQ ID No. 8 |
| An70-VWF Prot | SEQ ID No. 9 |
| An63-VWF Prot | SEQ ID No. 10 |
| cohVWF Prot | SEQ ID No. 11 |
| An60-VWF Prot | SEQ ID No. 12 |
| An61-VWF Prot | SEQ ID No. 13 |
| An62-VWF Prot | SEQ ID No. 14 |

TABLE 4-continued

| Correspondence between Sequence Names and SEQ ID Numbers | |
|---|---|
| Sequence Name | SEQ ID No. |
| An64-VWF Prot | SEQ ID No. 15 |
| An65-VWF Prot | SEQ ID No. 16 |
| An66-VWF Prot | SEQ ID No. 17 |
| An67-VWF Prot | SEQ ID No. 18 |
| An68-VWF Prot | SEQ ID No. 19 |
| An69-VWF Prot | SEQ ID No. 20 |
| An71-VWF Prot | SEQ ID No. 21 |
| An72-VWF Prot | SEQ ID No. 22 |
| An73-VWF Prot | SEQ ID No. 23 |
| An74-VWF Prot | SEQ ID No. 24 |
| An75-VWF Prot | SEQ ID No. 25 |
| An76-VWF Prot | SEQ ID No. 26 |
| An77-VWF Prot | SEQ ID No. 27 |
| An78-VWF Prot | SEQ ID No. 28 |
| An79-VWF Prot | SEQ ID No. 29 |
| An80-VWF Prot | SEQ ID No. 30 |
| An81-VWF Prot | SEQ ID No. 31 |
| An82-VWF Prot | SEQ ID No. 32 |
| An83-VWF Prot | SEQ ID No. 33 |
| An85-VWF Prot | SEQ ID No. 34 |
| An86-VWF Prot | SEQ ID No. 35 |
| An87-VWF Prot | SEQ ID No. 36 |
| An89-VWF Prot | SEQ ID No. 37 |
| An90-VWF Prot | SEQ ID No. 38 |
| An91-VWF Prot | SEQ ID No. 39 |
| An92-VWF Prot | SEQ ID No. 40 |
| An93-VWF Prot | SEQ ID No. 41 |
| An94-VWF Prot | SEQ ID No. 42 |
| An95-VWF Prot | SEQ ID No. 43 |
| An96-VWF Prot | SEQ ID No. 44 |
| An97-VWF Prot | SEQ ID No. 45 |
| An98-VWF Prot | SEQ ID No. 46 |
| An99-VWF Prot | SEQ ID No. 47 |
| An100-VWF Prot | SEQ ID No. 48 |
| An102-VWF Prot | SEQ ID No. 49 |
| An103-VWF Prot | SEQ ID No. 50 |
| An104-VWF Prot | SEQ ID No. 51 |
| An105-VWF Prot | SEQ ID No. 52 |
| An106-VWF Prot | SEQ ID No. 53 |
| An107-VWF Prot | SEQ ID No. 54 |
| An108-VWF Prot | SEQ ID No. 55 |
| An109-VWF Prot | SEQ ID No. 56 |
| An110-VWF Prot | SEQ ID No. 57 |
| An111-VWF Prot | SEQ ID No. 58 |
| An112-VWF Prot | SEQ ID No. 59 |
| An113-VWF Prot | SEQ ID No. 60 |
| An114-VWF Prot | SEQ ID No. 61 |
| An115-VWF Prot | SEQ ID No. 62 |
| An116-VWF Prot | SEQ ID No. 63 |
| An53-FVIII DNA | SEQ ID No. 64 |
| An68-FVIII DNA | SEQ ID No. 65 |
| An53-FVIII Prot | SEQ ID No. 66 |
| An84 -FVIII Prot | SEQ ID No. 67 |
| An68-FVIII Prot | SEQ ID No. 68 |
| An88-FVIII Prot | SEQ ID No. 69 |

SEQUENCE LISTING

The patent contains a lengthy sequence listing. A copy of the sequence listing is available in electronic form from the USPTO web site (https://seqdata.uspto.gov/?pageRequest=docDetail&DocID=US12116399B2). An electronic copy of the sequence listing will also be available from the USPTO upon request and payment of the fee set forth in 37 CFR 1.19(b)(3).

We claim:

1. A recombinant non-naturally occurring von Willebrand Factor (VWF) protein comprising the amino acid sequence of SEQ ID NO: 6 (An101-VWF), SEQ ID NO: 8 (An84-VWF), SEQ ID NO: 10 (An63-VWF), SEQ ID NO: 7 (An88-VWF) or SEQ ID NO: 9 (An70-VWF).

2. A nucleic acid encoding a recombinant non-naturally occurring VWF protein of claim 1.

3. A pharmaceutical composition comprising the nucleic acid of claim 2, and a pharmaceutically acceptable excipient.

4. A method of inducing blood clotting comprising administering an effective amount of the pharmaceutical composition of claim 3 to a subject in need thereof.

5. A composition comprising at least one recombinant non-naturally occurring von Willebrand Factor (VWF) protein of claim 1, and one artificial Factor VIII sequence or a Factor VIII sequence.

6. The composition of claim 5, wherein the artificial Factor VIII sequence is selected from SEQ ID NO: 66 to 69, or a combination thereof.

7. A method of inducing blood clotting comprising administering an effective amount of the composition of claim 5 to a subject in need thereof.

8. A method for treating a subject with a bleeding disorder, comprising administering an effective amount of the pharmaceutical composition of claim 3 to the subject.

9. The method of claim 8, wherein the subject is human.

10. The method of claim 8, wherein the bleeding disorder comprises hemophilia A or von Willebrand disease.

11. A pharmaceutical composition comprising the protein of claim 1, and a pharmaceutically acceptable excipient.

12. A method of inducing blood clotting comprising administering an effective amount of the recombinant non-naturally occurring von Willebrand Factor (VWF) protein of claim 1 to a subject in need thereof.

13. A method for treating a subject with a bleeding disorder, comprising administering an effective amount of the recombinant non-naturally occurring von Willebrand Factor (VWF) protein of claim 1 to the subject.

14. The method of claim 13, wherein the bleeding disorder comprises hemophilia A or von Willebrand disease.

* * * * *